United States Patent
Garrison

(10) Patent No.: US 7,550,151 B2
(45) Date of Patent: Jun. 23, 2009

(54) RENEWABLE TEXTURED COSMETIC COMPOSITIONS

(75) Inventor: Mark S. Garrison, Suffern, NY (US)

(73) Assignee: Avon Products, Inc., New York, NY (US)

( * ) Notice: Subject to any disclaimer, the term of this patent is extended or adjusted under 35 U.S.C. 154(b) by 443 days.

(21) Appl. No.: 10/743,615

(22) Filed: Dec. 22, 2003

(65) Prior Publication Data

US 2004/0136916 A1    Jul. 15, 2004

Related U.S. Application Data

(63) Continuation-in-part of application No. 09/989,745, filed on Nov. 20, 2001, now abandoned.

(51) Int. Cl.
*A61K 8/00* (2006.01)
*A61K 8/70* (2006.01)

(52) U.S. Cl. .................. 424/401; 424/59; 514/628

(58) Field of Classification Search ............... 424/401, 424/59
See application file for complete search history.

(56) References Cited

U.S. PATENT DOCUMENTS

| 2,859,085 | A | * | 11/1958 | Morrison | 215/12.1 |
| 6,224,851 | B1 | * | 5/2001 | Bara | 424/59 |
| 6,383,998 | B1 | | 5/2002 | Lorant | |
| 6,528,070 | B1 | * | 3/2003 | Bratescu et al. | 424/401 |

OTHER PUBLICATIONS

Tsutsumi et al, Whipped Cosmetics, Jun. 30, 1981, JP 56-79613 A, English translation.*
Occupational Safety & Health Administration Date (Chemical Sampling Information: Ethyl Perfluorobutyl Ether), Apr. 28, 1999, U.S. Department of Labor.*

* cited by examiner

*Primary Examiner*—Gina C. Yu
(74) *Attorney, Agent, or Firm*—Charles J. Zeller; Joan M McGillycuddy; Anthony M. Santini

(57) ABSTRACT

There is provided a cosmetic composition, preferably a cream, which continually provides a self-renewable textured surface appearance while in a container. The cosmetic composition has at least one volatile compound, preferably a fluorocarbon, such that the volatile compound expands resulting in expansion of the composition. The cosmetic composition has a viscosity from about 5,000 cps to about 2,500,000 cps.

22 Claims, No Drawings

RENEWABLE TEXTURED COSMETIC COMPOSITIONS

CROSS-REFERENCE TO A RELATED APPLICATION

The present application is a continuation-in-part application of parent application U.S. Ser. No. 09/989,745, filed Nov. 20, 2001 now abandoned, which is incorporated herein by reference in its entirety.

BACKGROUND OF THE INVENTION

I. Field of the Invention

The present invention relates to cosmetic compositions that may be packaged in a non-aerosol container, such as a jar. More particularly, the present invention relates to cosmetic creams or emulsions having at least one volatile compound that imparts a whipped texture to at least the upper portion of the cosmetic composition. Still more particularly, the textured surface of the cosmetic composition remaining in the container renews itself after each use of the composition by the consumer. In other words, the composition is "self-foaming" or "self-whipping" such that the surface thereof becomes re-texturized after each use during a pre-determined period of time.

II. Description of the Related Art

Foamable cosmetic compositions may take a variety of forms including, among others, skin and hair mousses, and aerosol shave foams. These prior art foaming products rely on gasses or "propellants" to produce the desired foaming characteristics. They also require special, highly pressurized packaging systems, such as metal aerosol spray cans, and elaborate dispensing systems involving valves, gaskets, fine mesh, etc. Furthermore, these systems use gasses that have relatively low flashpoints that are, thus, quite flammable and quite hazardous.

U.S. Pat. Nos. 6,210,656 and 6,033,647, assigned to L'Oreal, describe self-foaming compositions that are post foaming compositions (i.e., they foam after having been dispensed out of the container). Post-foaming compositions are packaged in pressurized aerosol containers and utilize flammable self-foaming agents. The flammability and volatility of these agents, and the pressure they build up in the container, make them impractical to be packaged in non-aerosol containers.

U.S. Pat. No. 5,500,211, assigned to Gillette, describes a self-foaming composition that is a post-foaming shaving composition, where the self-foaming agents are volatile hydrocarbons having 4 to 6 carbon atoms. These self-foaming agents are highly flammable. The flammability and volatility of these agents, and the pressure they build up in the container, make packaging such compositions in non-aerosol containers quite difficult, if not impossible.

U.S. Pat. No. 6,165,456, also assigned to Gillette, describes a self-foaming shaving gel comprising volatile hydrocarbons which, as discussed above, are flammable and, hence, potentially dangerous. Furthermore, such volatile hydrocarbons require the self-foaming shaving gel to be packaged in a suitable aerosol container.

U.S. Pat. Nos. 5,637,318; 5,643,601; 5,667,772; and 5,885,564, assigned to Lancaster, provides the use of an oxygen laden fluorocarbon to help transport oxygen through the skin. The fluorocarbon of choice is mixed with oxygen in a pressurized vessel, so that the oxygen is dissolved and "loaded" into the fluorocarbon and, thus, the final compositions.

U.S. Pat. No. 6,113,919, assigned to Alliance Pharmaceutical, discloses a partially fluorinated hydrocarbon having a lipophilic portion between 4 and 18 carbon atoms to help enhance the particle size stability of a fluorocarbon.

U.S. Pat. No. 5,741,499, assigned to L'Oreal, describes a homogeneous solution containing specially modified fluorinated compounds and glycols. The fluorinated compounds have at least one functional group consisting of alcohol, thiol, or primary or secondary amine to associate with glycols in the formula, thus enabling a homogeneous solution. The present invention, in contrast, uses fluorocarbons, which are substantially free of alcohol, thiol, or amine functionality, and preferably contain none.

U.S. Pat. No. 6,251,375, also assigned to L'Oreal, provides for the use of volatile fluorinated compounds to accelerate the drying time of make-up, nail care, and suncare compositions. However, this patent fails to provide a self-foaming composition, which is able to produce a renewable, whipped surface texture, and which can be packaged in a non-aerosol container.

U.S. Pat. No. 6,224,851, also assigned to L'Oreal, provides a process for making transfer resistant make-up or sunscreen cosmetic compositions containing particles of a pigment or filler, by introducing at least one volatile fluorinated solvent in a sufficient amount to act as an anti-transfer agent. However, this patent fails to provide a self-foaming composition, which is able to produce a renewable, whipped surface texture, and which can be packaged in a non-aerosol container.

Also known in the art are methods to produce foamed products that require packages that dispense compositions as a foam using specialized dispensers. Although these containers are non-aerosol containers, they require that the product passes through a fine mesh as it is pump dispensed to give a foamed appearance. These mesh-foam packages work well with only very thin products, i.e., having viscosities of less than about 1000 centipoise.

In short, the prior art fails to teach the use of volatile fluorocarbons having suitable volatility (vapor pressure and/or boiling point) parameters as self-foaming agents, or their use to create a renewable, whipped surface texture to a cosmetic product packaged in a conventional jar. There is a need in the art for such a whipped/foamed product that can be packaged in a non-aerosol container, saving the cost and filling requirements of using pressurized aerosol cans/packaging, and which uses a safe, non-flammable ingredient to produce the foamed/whipped texture.

SUMMARY OF THE INVENTION

It is an object of the present invention to provide a container having a cosmetic cream with a volatile compound in which the composition self-attains a renewable, textured surface after each use while in the container.

It is another object of the present invention to provide self-foaming compositions, which can be packaged and sold commercially in a container, such as a jar, so that after each use, the aesthetic appeal of the whipped surface texture can be self-renewed after the jar is capped for a pre-determined period of time.

It is still another object of the present invention to achieve the above desired effect without the use of a flammable foaming agent, such as a hydrocarbon gas.

It is a further object of the present invention to provide a cosmetic cream in which the self-foaming agent additionally imparts a cooling sensation to the skin when the cream is applied.

It is still a further object of the present invention to provide such a cosmetic cream in which the self-foaming action occurs at a sufficient rate that the consumer has an indication, e.g. see and hear the process occur to some degree, when they examine or apply the cream.

To accomplish the foregoing objects and advantages, the present invention, in brief summary, is a cosmetic composition that has a volatile compound, such that, while in its container, the volatile compound, and thus the composition, expands resulting in the composition having a renewable textured surface. The composition preferably is an emulsion. Also, the composition has a viscosity from about 5,000 cps (centipoise) to about 2,500,000 cps.

DETAILED DESCRIPTION OF THE INVENTION

The present invention is a cosmetic composition having a textured surface appearance that is self-renewed after each use. The composition is most preferably a cream. The cream is preferably contained in a non-aerosol, re-sealable container, such as, for example, a tube, a bottle, jar or non-pressurized metal container. The upper portion of the cream has a textured appearance in the container. This textured appearance is analogous to the look of foam/bubbles, and/or nooks/crannies/craters. The appearance may also be described as "foamed" or "whipped". Each time that a portion of the cream is removed from the container, such that the surface of the cream is disturbed or altered by, for example, a consumer's fingers/fingertips or some other manual applicator, the impressions or disturbances caused by the consumer's fingers/fingertips or other applicator become quickly obscured by the foaming caused by the present composition. Thus, the original, non-disturbed textured surface appearance of the composition in the container reappears or is renewed within a relatively short period of time after the container is re-sealed, sometimes within as little as about 2 hours, typically from about 2 hours to about 24 hours, and certainly after weekly use.

In other words, when a jar of cosmetic cream is opened for the first time, it has a nicely finished, leveled, aesthetically appealing, foamy or whipped appearance. However, after the very first use, and every time thereafter that a consumer dips her fingers into the jar, the surface of the cream typically remains with troughs, furrows and other concavities. The present invention provides for a cosmetic composition that self-levels and self-whips/self-foams its surface appearance during a pre-determined period of time after each use, such that each subsequent time that the jar is re-opened, the surface appearance of the composition (which ordinarily would have troughs, furrows and other concavities made in it) has renewed itself and looks like it did just before each use. For a product that is used daily, and renews itself within that timeframe, this effect is novel and exciting, since the surface texture will appear newly whipped and re-leveled each time the jar is opened.

The cosmetic composition of the present invention has a self-foaming agent, preferably a volatile compound. The self-foaming agent expands due to its tendency to volatilize and, thus, causes the composition to also expand and foam, thereby imparting a re-textured surface appearance to the composition. This unique attribute is made possible by the addition of a volatile compound effective to cause the cosmetic composition to renew its original textured surface appearance. In other words, the volatile compound builds up sufficient pressure to re-foam/re-whip the surface of the composition, but not so much pressure that it needs to be contained in a pressurized metal container.

The composition of the present invention has a viscosity effective to permit expansion of the self-foaming agent. The viscosity of the composition should be adequate enough to maintain the whipped textured surface once it is formed, yet also thick enough so that it can be packaged in a jar without running. The viscosity of the composition is from about 5,000 cps to about 2,500,000 cps, more preferably about 50,000 cps to about 1,500,000 cps, still more preferably about 100,000 cps to about 1,000,000 cps, and most preferably about 250,000 cps to about 750,000 cps. Other useful composition viscosities are from about 5,000 cps to about 500,000 cps, more preferably from about 10,000 cps to about 200,000 cps, even more preferably from about 20,000 cps to about 100,000 cps, and most preferably from about 35,000 cps to about 75,000 cps.

Preferably, the volatile compound of the present invention also has a suitable latent heat of evaporation such that it produces a cooling sensation on the surface of skin when the composition is applied. Depending on the self-foaming agent chosen, this cooling sensation can be accompanied by a bubbly or fizzy sound or sensation.

Volatile compounds that are at least partially fluorinated exhibit the best chemical characteristics to facilitate the self-foaming behavior of the present invention. The greater the number of carbon-fluorine bonds in the molecule, the greater this desirable behavior. For foaming efficiency (i.e. most foaming for least amount of foaming agent needed), the best compounds for this purpose consist entirely of carbon and fluorine atoms, and thus contain only carbon-carbon and carbon-flourine bonds. For partially fluorinated compounds, the remainder of the molecule preferably has carbon-hydrogen, carbon-oxygen, and carbon-carbon bonds. Additionally, and most preferably, the absence of additional functional groups, such as amine, alcohol, acid (including carboxylic acid), thiol, silicone, ester, and amide minimizes any possible affinity for other components in the cosmetic composition, which could decrease the ability of the composition to renew its textured surface appearance.

The preferred volatile compound for use in the present invention is a fluorocarbon. We define fluorocarbon as a compound containing fluorine and carbon, but which can contain other atoms as well. Useful fluorocarbons include perfluorocarbons, such as the perfluoroalkylcycloalkanes and hydrofluoroethers. Examples of perfluoroalkylcycloalkanes include perfluoromethyl-cyclopentane and perfluouromethylcyclohexane. Examples of hydrofluoroethers include methyl perfluorobutyl ether, methyl perfluoroisobutyl ether, ethyl perfluorobutyl ether, and ethyl perfluoroisobutyl ether. Mixtures of methyl perfluorobutyl ether and methyl perfluoroisobutyl ether are available as CF-61 (formerly known as Novec HFE 7100) sold by the 3M Company. Mixtures of ethyl perfluorobutyl ether and ethyl perfluoroisobutyl ether are available as CF-76 (formerly known as Novec HFE 7200) sold by the 3M Company. The hydrofluoroethers are highly preferred in the present invention.

Perfluoromethylcyclohexane is an organic compound that has the formula:

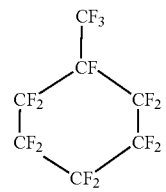

This perfluoromethylcyclohexane is available under the trade name Flutec PP2 or Flutec PC2 (F2 Chemicals Ltd.).

The compound perfluoromethyl cyclopentane is available under the trade name Flutec PC1C (F2 Chemicals Ltd.). It has the following formula:

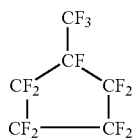

Also suitable for use as a volatile compound in the present invention are perfluorohexane and perfluorodimethylcyclohexane, available under the tradenames Flutec PC1 and Flutec PC3 (F2 Chemicals Ltd.), respectively. Perfluorodimethylcyclopentane (molecular weight of about 350) is also expected to be suitable in the present invention.

The fluorocarbon compounds of the present invention preferably have a boiling point from about 45 degrees C. to about 110 degrees C., and more preferably from about 65 degrees C. to about 85 degrees C. Related to the boiling point is the vapor pressure of the compound at room temperature (25 degrees C.). The vapor pressure at room temperature is a measure of the volatility of the compound. The more viscous the composition, the higher the vapor pressure required to produce a whipped texture in the surface of the composition. Preferably, the vapor pressure at room temperature should be from about 20 mbar to about 500 mbar, more preferably from about 100 mbar to about 300 mbar. These boiling point and vapor pressure parameters apply preferably to any volatile compound used in the present invention.

The volatile compound of the present invention is present in the composition in an amount from about 0.01 to about 25 wt % (weight percent), preferably about 0.1 to about 3 wt %, more preferably about 0.2 wt % to about 1.0, and most preferably about 0.25 wt % to less than 0.5 wt %, based on the total weight of the composition. Other useful amount levels for the volatile compound are from about 1% to about 15%, and preferably about 2.5 wt % to about 10 wt %, based on the total weight of the composition.

The cosmetic composition of the present invention is preferably an emulsion, more preferably an oil-in-water emulsion. Most preferably, the composition is an oil-in-water cream. The emulsion may also be water-in-oil, water-in-silicone or a multiple emulsion. Ideally, the self-foaming agent should not totally dissolve into any phase of the emulsion, but rather when mixed into the emulsion should be present somewhat as tiny droplets of its own third phase.

Suitable cosmetic creams include, but are not limited to, a facial cream, a body cream, a facial mask, a cleansing cream, a hair conditioning crème, a crème shampoo, or a shaving cream.

Preferred cream and lotion compositions have a surfactant and/or a soap. Preferred soaps are fatty acid soaps, such as those of behenic acid, stearic acid, palmitic acid, myristic acid, lauric acid, coconut acid (known as cocoates), and other such acids. The fatty acids are neutralized with a suitable base, such as triethanolamine, sodium hydroxide or potassium hydroxide, to form the soap. The use of these soaps in the compositions is advantageous because they provide both foaming and body to the composition. The fatty acid soaps give viscosity to the composition, and since soap systems typically (but not necessarily) contain some non-neutralized fatty acid, this provides further viscosity and crème consistency to the composition. Non-neutralized fatty acid also produces a pearlized effect in the composition that is very aesthetic. This pearlized effect is due to tiny crystals of fatty acid forming in the composition, which manifest themselves as a pearlescent appearance. This pearlized effect typically develops over time in the composition, usually within about a month, and is normally accompanied by a loss of viscosity. Useful surfactants include, by way of example, sodium methyl cocoyl taurate and sodium lauryl sulfate, and serve to enhance the foaming of the composition.

Preferred compositions have soaps present from about 1 wt % to about 50 wt %. More preferred compositions have soaps present from about 15 wt % to about 40 wt %. Most preferred compositions have soaps present from about 25 wt % to about 35 wt %.

The cosmetic composition of the present invention can include other suitable components, such as one or more foam-modifying agents. For example, cyclomethicone, which is miscible with fluorinated liquids, can be incorporated into the composition in order to modify or attenuate the foaming characteristics. Another class of compounds that can be used to modify the foaming characteristics are higher molecular weight compounds that also contain fluorine. Accordingly, silicones that are partially fluorinated, polymeric hydrocarbons that are partially fluorinated, amines that are partially fluorinated, alcohols that are partially fluorinated, in fact any class of compound that is partially fluorinated, can help to dissolve the self-foaming liquid into one of the phases in the emulsion, thus influencing its foaming characteristics by decreasing the foaming behavior at room temperature. Substances such as the Fomblins, a class of perfluorinated ether polymers, are also suitable for this purpose. Also, higher molecular weight, nonvolatile compounds of the Flutec products disclosed above can also be used as modifiers of the foaming characteristics of the composition.

The foam-modifying agent is preferably present in an amount from about 0.1 wt % to about 60 wt % based on the total weight of the composition. More preferably, the foam-modifying agent is present in an amount from about 2 wt % to about 25 wt % based on the total weight of the composition.

The cosmetic compositions of the present invention may also have one or more thickening agents. The presence of, for example, a polymeric thickening agent, helps to stabilize the whipped appearance of the composition, and stabilize the uniform dispersion of the droplets of foaming agents in the composition. Also, because the density of the self-foaming agent is substantially greater than that of the composition, it has a tendency to sink to the bottom of low viscosity systems, which can have a detrimental effect on the foaming effect. Thus, the use of polymeric thickening agents and/or thickening agents capable of producing rheological "yield value" is especially useful. Useful polymeric thickening agents include, but are not limited to, polyacrylic acid polymers known as carbomers, polyacrylamide polymers such as Seppigel, and other polymers based on acrylamide or acrylic acid. Also useful are cellulose and starch derivatived thickeners, and other polysaccharide derived thickeners. Examples of these thickeners include, but are not limited to, xanthan gum, carageenan, hydroxyethyl cellulose, gellan gum, hydroxypropyl methylcellulose, chitosan, hyaluronic acid, and modified starches such as those sold under the trade name Solnace. Also useful are inorganic thickening agents, such as magnesium aluminum silicate, sodium aluminum silicate, and fumed silica. Waxes are also useful as thickeners to add body and viscosity. Examples of waxes include, but are not limited to, glyceryl monostearate, stearic acid, and ethylene glycol mono and distearates. Some of these waxes can serve a dual purpose, e.g. to thicken and to provide an attractive pearlescent appearance in the product that develops over time.

The thickening agent is preferably present in an amount from about 0.01 wt % to about 5 wt % based on the total weight of the composition. More preferably, the thickening agent is present in an amount from about 0.5 wt % to about 2.0 wt % based on the total weight of the composition.

Also useful in the formulation are nonionic emulsifying agents. These add stability to the composition and contribute towards a uniform white appearance to the composition, which is perceived as attractive when combined with the self-whipping texture.

The cosmetic composition may also have one or more emollients, humectants, emulsifiers, preservatives, chelating agents, sunscreen agents, water proofing agents vitamins, botanical extracts, insect repellents, fragrances, film formers, active ingredients (such as, for example, anti-acne ingredients or skin whitening ingredients), solubilizing agents, exfoliating agents, or any combinations thereof.

Useful in the manufacture of self-foaming emulsions is a homogenizer or other high shear device. These aid in the uniform dispersion of the self-foaming agent, which ideally is incorporated rapidly into the composition, and ideally processed in a vessel with a minimum of headspace. Preferably, when the composition is an emulsion, the emulsion is prepared first and the self-foaming agent is then added to the emulsion as the last ingredient. This assists in distributing the self-foaming agent throughout the composition as its own phase.

The preferred embodiments of the present invention are suitable to be packaged in any number of typical cosmetic containers, such as metal or plastic tubes, or, more preferably, jars with caps. The cap of a container effectively substantially seals the composition against any escape of pressure built up in the container. The embodiments that use the most volatile self-foaming agents are preferably packaged in a container having a cap that maintains a very airtight and robust seal, such that the foaming composition does not leak out under high temperature conditions when the composition is not in use.

As the cosmetic composition is used by a consumer, the headspace in the container will gradually increase over time as the amount of the cosmetic composition in the package decreases. To some extent, it will be refilled with freshly re-foamed composition but, after numerous openings, depending on the specific composition viscosity or soap level, the foaming agent used and the container, the foaming response will not disappear, but may become less vigorous. Thus, an ideal container for this type of cream would be one where the bottom is engineered to have an adjustable inner volume, such as, for example, to swivel and "dial up", as in some current containers used for stick or deodorant products. This would help minimize the headspace, so that the base can be elevated slightly after each use, to help minimize the composition going "flat". Such a container is not necessary but would be desirable, particularly in a jar-type configuration.

The compositions of the present invention have significant aesthetic benefits. In particular, each composition has a self-renewing surface appearance that is similar to whipped cream or foam texture. After each use, such that a portion of the cream is removed from the container by the consumer's fingers/fingertips, the impressions and other disturbances created in the surface of the composition begin to obscure and re-level, such that the textured surface of the cream reappears in the container within a brief period of time after the container is sealed. This continual, renewable, textured surface appearance is believed aesthetically pleasing to a consumer.

Moreover, when the container is opened, some of the foam bubbles pop, creating a bubbling or fizzy sound. This effect is aesthetically different and interesting in a cream, and it is believed that it too will be viewed as positive by the consumer.

The following are examples of the compositions of the present invention:

EXAMPLE I

Compositions 1 and 2 were identically formulated, except Composition 1 (the invention) contained 2.5% Flutec PC2 and Composition 2 contained 2.5% ethanol. Flutec PC2 has a boiling point (BP) of 76 degrees C. and ethanol has a boiling point of 78.5 degrees C.

The boiling points are similar, yet the behavior of these two compositions is totally diverse. Composition 1 (the invention) gives a substantial foaming effect, creating a very aesthetic whipped cream-like appearance. Composition 2 produces no foaming. This is because the ethanol molecules, although being of a similar BP to the Flutec PC2, hydrogen-bond to the aqueous phase of the composition, and dissolve completely in the composition. The OH group on ethanol can also hydrogen-bond to other polar groups of other ingredients in the composition. Also, the remainder of the ethanol molecule is hydrocarbon, and so can bond with other organic components in the system. Since the ethanol is totally solvated in this system, it behaves differently from the volatile compound of the present invention. Thus, the ethanol does not produce a foamed or whipped appearance on the surface of the composition.

|  | Composition 1 (Invention) | Composition 2 (Comparison) |
|---|---|---|
| Ethanol | 0 | 2.5 |
| Perfluoromethylcyclohexane (Flutec PC2) | 2.5 | 0 |
| Xanthan Gum | 0.5 | 0.5 |
| Disodium EDTA | 0.2 | 0.2 |
| Dimethicone | 2 | 2 |
| Hyaluronic acid | 0.01 | 0.01 |
| Stearic acid | 1.25 | 1.25 |
| Magnesium aluminum silicate | 0.5 | 0.5 |
| Cetearyl alcohol | 6 | 6 |
| Cetyl ricinoleate | 3 | 3 |
| C12-15 alkyl benzoate | 2 | 2 |
| Octylmethoxycinnamate | 7.5 | 7.5 |
| Benzophenone-3 | 3.5 | 3.5 |
| Butylmethoxydibenzoylmethane | 2 | 2 |
| Choleth-24 | 0.5 | 0.5 |
| IR-3535 | 5 | 5 |
| Zeolite | 0.25 | 0.25 |
| Propylene glycol | 2 | 2 |
| Pentylene glycol | 2 | 2 |
| Benzyl alcohol | 1 | 1 |
| Polysorbate 60 | 0.5 | 0.5 |
| Steareth-20 | 0.25 | 0.25 |
| Peg 100 stearate | 0.5 | 0.5 |
| Tocopheryl acetate | 0.1 | 0.1 |
| Fragrance | 0.2 | 0.2 |
| Methyl paraben | 0.35 | 0.35 |
| Water | qs to 100 | qs to 100 |

EXAMPLE II

Cosmetic Compositions 3 and 4 were identically formulated, except Composition 3 (the invention) contained 2.5% Flutec PC2 and Composition 4 contained 2.5% perfluorodecalin (Flutec PP5). Flutec PC2 has a boiling point of 76 degrees C. and perfluorodecalin has a boiling point of 142 degrees C.

Even though both ingredients are perfluorocarbons, it was determined that only Composition 3 (the invention), containing 2.5% perfluoromethylcyclohexane, will produce an attractive whipped appearance, whereas Composition 4, containing perfluorodecalin, will not. The chemical nature of these two compounds being equal, and the cream bases being the same, the whipping/foaming is here influenced by the relative volatility of these two compounds, as illustrated by their relative boiling points.

|  | Composition 3 (Invention) | Composition 4 (Comparison) |
| --- | --- | --- |
| Perfluoromethylcyclohexane (Flutec PC2) | 2.5 | 0 |
| Perfluorodecalin (Flutec PP5) | 0 | 2.5 |
| Carbopol 934 | 0.7 | 0.7 |
| Disodium EDTA | 0.2 | 0.2 |
| Glycerin | 3 | 3 |
| Cyclomethicone | 10 | 10 |
| Octyl methoxy cinnamate | 7.5 | 7.5 |
| Benzophenone-3 | 3 | 3 |
| Butylmethoxydibenzoylmethane | 2 | 2 |
| Sodium hydroxide solution | 0.5 | 0.5 |
| Botanical extracts | 2 | 2 |
| Fragrance | 0.3 | 0.3 |
| Methyl paraben | 0.3 | 0.3 |
| Benzyl alcohol | 1 | 1 |
| PEG-100 stearate | 1.25 | 1.25 |
| Laureth-4 | 0.5 | 0.5 |
| Cetyl alcohol | 0.1 | 0.1 |
| Water | qs to 100 | qs to 100 |

EXAMPLE III

The following composition can be prepared:

| Fatty Acids (i.e. stearic, palmitic, lauric, etc.) | 30 wt % |
| --- | --- |
| Potassium Hydroxide (45%) | 10.5 wt % |
| Sodium Methyl Cocoyl Taurate (30%) | 5 wt % |
| Polyol (i.e. polyethylene glycol) | 5 wt % |
| Preservative | as needed |
| Fragrance | as needed |
| CF-61 | 0.2-0.4 wt % |
| Water | qs to 100 wt % |

The viscosity of the composition of Example III is approximately 900,000 centipoise when manufactured. Upon aging about 1 month at ambient temperature, the above composition is approximately 400,000 centipoise.

Having thus described the present invention with particular reference to preferred embodiments thereof, it will be apparent that various changes and modifications may be made therein without departing from the spirit and scope of the present invention as defined in the appended claims.

What is claimed is:

1. A system, comprising:
a non-aerosol, re-sealable container, the container comprising a jar that permits a user's fingers to be dipped into said composition and which permits the user to see the surface of the composition contained therein when the jar is opened; and (ii) a cap for said jar, the cap being sealable with and removable from the jar; and
a composition having a textured surface appearance and being situated within the container that builds up pressure when sealed and releases pressure when opened, the composition having a volatile compound in an amount effective to renew the textured surface appearance after the surface has been disturbed and after the container has been sealed against escape of pressure by the cap, the composition having a viscosity from about 35,000 cps to about 1,500,000 cps, the composition being an oil-in-water emulsion, the emulsion having an emulsifier,
wherein the volatile compound has a vapor pressure about 20 mbar to about 500 mbar at 25 degrees C. and a boiling point from about 45 degrees C. to about 85 degrees C.,
wherein the volatile compound does not totally dissolve in either the oil phase or the water phase,
wherein the volatile compound has one or more perfluorobutyl ethers present in an amount from about 0.1% to about 3% by total weight of the composition, and
wherein the composition is in the form of a cream.

2. The system of claim 1, wherein the viscosity is about 35,000 cps to about 500,000 cps.

3. The system of claim 1, wherein the viscosity is about 50,000 cps to about 1,500,000 cps.

4. The system of claim 1, wherein the viscosity is about 100,000 cps to about 1,000,000 cps.

5. The system of claim 1, wherein the viscosity is about 250,000 cps to about 1,500,000 cps.

6. The system of claim 1, wherein the viscosity is about 35,000 cps to about 200,000 cps.

7. The system of claim 1, wherein the viscosity is about 35,000 cps to about 75,000 cps.

8. The system of claim 1, wherein the composition is maintained in the container for a period of about 2 hours to about 24 hours after each use.

9. The system of claim 1, wherein the container has an adjustable inner volume.

10. The system of claim 1, wherein the one or more perfluorobutyl ethers is selected from the group consisting of methyl perfluorobutyl ether, methyl perfluoroisobutyl ether, ethyl perfluorobutyl ether, ethyl perfluoroisobutyl ether, and any combinations thereof.

11. The system of claim 1, wherein the volatile compound has a vapor pressure about 100 mbar to about 300 mbar at 25 degrees C.

12. The system of claim 1, wherein the volatile compound has a boiling point about 45 degrees C. to about 85 degrees C.

13. The system of claim 1, wherein the volatile compound has a boiling point about 65 degrees C. to about 85 degrees C.

14. The system of claim 1, wherein the volatile compound is present in an amount about 0.2 wt % to about 1 wt % by total weight of the composition.

15. The system of claim 1, wherein the volatile compound is present in an amount about 0.25 wt % to less than 0.5 wt % by total weight of the composition.

16. The system of claim 1, wherein the volatile compound is present in an amount about 2.5 wt % to about 10 wt % by total weight of the composition.

17. The system of claim 10, wherein the viscosity is about 35,000 cps to about 500,000 cps.

18. A method of imparting a self-renewing and self-leveling textured surface appearance to a composition after each use, the composition having a volatile compound with a vapor pressure from about 20 mbar to about 500 mbar at 25 degrees C. and a boiling point from about 45 degrees C. to about 85 degrees C., the composition being an emulsion having an oil phase and a water phase, the volatile compound not totally dissolving in either the oil phase or the water phase, the emulsion being an oil-in-water emulsion, the emulsion having an emulsifier, the volatile compound being one or more perfluorobutyl ethers present in an amount about 0.1% to about 3% by total weight of the composition, the composition being in the form of a cream, the composition having a viscosity of from about 35,000 cps to about 1,500,000 cps, the method comprising:

providing the composition in an amount effective for enabling such self-renewing and self-leveling appearance in a non-aerosol, re-sealable container, the container comprising a jar that permits a user's fingers to be dipped into said composition and which permits the user to see the surface of the composition contained therein when the jar is opened, said jar having a removably sealable cap effective to seal the composition against escape of pressure, and maintaining the composition in a capped state for a pre-determined period of time after each use to allow the composition to self-renew and self-level the textured surface appearance of the composition.

19. The system of claim 18, wherein the viscosity is about 35,000 cps to about 500,000 cps.

20. The method of claim 18, wherein the hydrofluoroether is present in an amount about 0.25 wt% to less than 0.5 wt% by total weight of the composition.

21. The method of claim 18, wherein the composition is maintained in the container for a period of about 2 hours to about 24 hours after each use.

22. A method of leveling surface appearance of a cream composition after each use of the composition, the method comprising:

including in the composition a volatile compound having a vapor pressure from about 20 mbar to about 500 mbar and a boiling point from about 45 degrees C. to about 85 degrees C. and providing the composition with a viscosity from about 35,000 cps to about 1,500,000 cps, the composition being an emulsion having an oil phase and a water phase, the volatile compound not totally dissolving in either the oil phase or the water phase, the emulsion being an oil-in-water emulsion, the emulsion having an emulsifier, the volatile compound being one or more perfluorobutyl ethers present in an amount about 0.1% to about 3% by total weight of the composition, the composition being in the form of a cream; and situating the composition in a non-aerosol, re-sealable container, the container comprising a jar that permits a user's fingers to be dipped into said composition and which permits the user to see the surface of the composition contained therein when the jar is opened, said jar having a removable and sealable cap that seals against escape of pressure for a pre-determined period of time after each use, wherein the surface appearance of the composition self-levels during such pre-determined period of time.

\* \* \* \* \*